United States Patent
Johansen

(10) Patent No.: US 9,891,203 B2
(45) Date of Patent: Feb. 13, 2018

(54) SWATH# DATA-INDEPENDENT ACQUISITION TECHNOLOGY FOR THE DETECTION OF HOST CELL PROTEIN CONTAMINANTS IN BIOTHERAPEUTICS PROTEIN PRODUCTS

(71) Applicant: DH TECHNOLOGIES DEVELOPMENT PTE. LTD., Singapore (SG)

(72) Inventor: Eric Johansen, Oakland, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/889,138

(22) PCT Filed: Jun. 3, 2014

(86) PCT No.: PCT/IB2014/000940
§ 371 (c)(1),
(2) Date: Nov. 4, 2015

(87) PCT Pub. No.: WO2014/195783
PCT Pub. Date: Dec. 11, 2014

(65) Prior Publication Data
US 2016/0109424 A1      Apr. 21, 2016

Related U.S. Application Data

(60) Provisional application No. 61/831,582, filed on Jun. 5, 2013.

(51) Int. Cl.
*G01N 24/00* (2006.01)
*G01N 33/00* (2006.01)
(Continued)

(52) U.S. Cl.
CPC ......... *G01N 33/15* (2013.01); *G01N 30/7233* (2013.01); *G01N 33/6848* (2013.01); *H01J 49/0072* (2013.01); *H01J 49/004* (2013.01)

(58) Field of Classification Search
CPC ............... G01N 33/15; G01N 30/7233; G01N 33/6848; G01N 24/00; G01N 33/00
(Continued)

(56) References Cited

U.S. PATENT DOCUMENTS

| 7,197,402 B2 | 3/2007 | Mistrik | |
|---|---|---|---|
| 2013/0124102 A1* | 5/2013 | Tate | G06F 17/00 702/22 |

(Continued)

FOREIGN PATENT DOCUMENTS

WO    2012035412 A2    3/2012

OTHER PUBLICATIONS

International Search Report and Written Opinion for PCT/IB2014/000940, dated Sep. 25, 2014.
(Continued)

*Primary Examiner* — Brian J Sines
(74) *Attorney, Agent, or Firm* — John R. Kasha; Kelly L. Kasha; Kasha Law LLC

(57) ABSTRACT

Systems and methods are provided for detecting host cell contaminants in a protein biotherapeutic product using sequential windowed acquisition tandem mass spectrometry. Sequential windowed acquisition is performed on a protein biotherapeutic product sample by sequentially stepping a precursor mass window across a mass range, fragmenting transmitted precursor ions of each stepped precursor mass window, and analyzing product ions produced from the fragmented transmitted precursor ions. The sequential windowed acquisition is performed without any information about contaminating proteins before data acquisition, and (Continued)

produces data for every product ion of every transmitted precursor ion for the mass range. One or more measured product ion spectra are received, and compared to a library of host cell proteins. One or more host cell contaminants are detected by reporting host cell proteins from the library that match the one or more measured product ion spectra.

7 Claims, 10 Drawing Sheets

(51) Int. Cl.
  *G01N 33/15* (2006.01)
  *G01N 33/68* (2006.01)
  *G01N 30/72* (2006.01)
  *H01J 49/00* (2006.01)

(58) Field of Classification Search
  USPC ......... 422/50, 68.1; 436/43, 173, 86, 87, 89, 436/90, 94
  See application file for complete search history.

(56) References Cited

U.S. PATENT DOCUMENTS

| | | | |
|---|---|---|---|
| 2013/0206979 A1* | 8/2013 | Bonner | H01J 49/0031 250/282 |
| 2015/0248998 A1* | 9/2015 | Tate | H01J 49/0036 702/19 |

OTHER PUBLICATIONS

Doneanu et al., "Analysis of Host-Cell Proteins in Biotherapeutic Proteins by Comprehensive Online Two-Dimensional Liquid Chromatography/Mass Spectrometry," Landes Bioscience, 2012, vol. 4, No. 1, pp. 24-44.

Nesvizhskii et al., "A Statistical Model for Identifying Proteins by Tandem Mass Spectrometry," Analytical Chemistry, 2003, vol. 75, No. 17, pp. 4646-4658.

Geromanos et al., "The detection, Correlation, and Comparison of Peptide Precursor and Product Ions from Data Independent LC-MS with Data Dependant LC-MS/MS," Proteomics, 2009, vol. 9, No. 6, pp. 1683-1695.

Schenauer et al., "Identification and Quantification of Host Cell Protein Impurities in Biotherapeutics Using Mass Spectrometry," Analytical Biochemistry, 2012 vol. 428, No. 2, pp. 150-157.

Gillet et al. "Targeted Data Extraction of the MS/MS SPectra Generated by Data-Independent Acquisition: A New Concept for Consistent and Accurate Proteome Analysis," Molecular and Cullular Proteomics, vol. 11, No. 6, Jan. 18, 2012.

Sidoli et al. "Sequential Window Acquisition of all Theoretical Mass Spectra (SWATH) Analysis for Characterization and Quantification of Histone Post-Translational Modifications," Molecular & Cellular Proteomics, vol. 14, No. 9, Jan. 30, 2015.

Doneanu et al. "Analysis of Host-Cell Proteins in Biotherapeutic Proteins by Comprehensive Online Two-dimensional Liquid Chromatography/Mass Spectrometry," MABS (Taylor & Francis Group Publishers), vol. 4, No. 1, Jan. 1, 2012.

* cited by examiner

SWATH# DATA-INDEPENDENT ACQUISITION TECHNOLOGY FOR THE DETECTION OF HOST CELL PROTEIN CONTAMINANTS IN BIOTHERAPEUTICS PROTEIN PRODUCTS

CROSS REFERENCE TO RELATED APPLICATION

This application claims the benefit of U.S. Provisional Patent Application Ser. No. 61/831,582, filed Jun. 5, 2013, the content of which is incorporated by reference herein in its entirety.

INTRODUCTION

Monoclonal antibodies (mAb) are target-oriented biotherapeutics that are used to treat an array of human diseases. mAbs are typically produced in biological systems, such as Chinese hamster ovary (CHO) or other cell lines. Heterogeneity of IgG proteins due to post-translational modifications (PTMs), sequence variants, degradation products, and contaminants (such as host cell proteins) must be characterized completely to understand purity, stability and potency of the mAb product, and to avoid immunogenicity.

Current methods for the detection of host cell protein contaminants in protein biotherapeutic products, such as non-data-independent acquisition (DIA) mass spectrometry methods, discovery proteomics methods, and multiple reaction monitoring (MRM), rely heavily on secondary reagents to detect them. Specifically, the host cell is lysed and a polyclonal antibody is developed by injecting the lysate into a rabbit or other small animal. This antibody is then used in an enzyme-linked immunosorbent assay (ELISA) assay to detect if any host cell proteins have traveled through purification processes alongside the protein biotherapeutics after it is grown inside the host cell. A major assumption in this dogma is that rabbit and human will have similar immune response to any host cell protein that is injected into their bloodstream. It turns out that this assumption is not always true, and many biopharmaceutical companies are facing challenges from host cell proteins that did not produce a reaction in the rabbit, but cause a problematic response in human patients.

SUMMARY

A system is disclosed for detecting host cell contaminants in a protein biotherapeutic product using sequential windowed acquisition tandem mass spectrometry. The system includes a tandem mass spectrometer and a processor. The tandem mass spectrometer performs sequential windowed acquisition on a protein biotherapeutic product sample by sequentially stepping a precursor mass window across a mass range, fragmenting transmitted precursor ions of each stepped precursor mass window, and analyzing product ions produced from the fragmented transmitted precursor ions. The sequential windowed acquisition is performed without receiving any information about contaminating proteins before data acquisition. The sequential windowed acquisition produces a plurality of product ion spectra for the mass range.

The processor receives one or more measured product ion spectra of the plurality of product ion spectra from the tandem mass spectrometer, compares the one or more measured product ion spectra to a library of host cell proteins, and detects one or more host cell contaminants by reporting host cell proteins from the library that match the one or more measured product ion spectra.

A method is disclosed for detecting host cell contaminants in a protein biotherapeutic product using sequential windowed acquisition tandem mass spectrometry. Sequential windowed acquisition is performed on a protein biotherapeutic product sample using a tandem mass spectrometer. The sequential windowed acquisition is performed by sequentially stepping a precursor mass window across a mass range, fragmenting transmitted precursor ions of each stepped precursor mass window, and analyzing product ions produced from the fragmented transmitted precursor ions. The sequential windowed acquisition is performed without any information about contaminating proteins before data acquisition. The sequential windowed acquisition produces a plurality of product ion spectra for the mass range.

One or more measured product ion spectra of the plurality of product ion spectra are received from the tandem mass spectrometer using a processor. The one or more measured product ion spectra are compared to a library of host cell proteins using the processor. One or more host cell contaminants are detected by reporting host cell proteins from the library that match the one or more measured product ion spectra using the processor.

A computer program product is disclosed that includes a non-transitory and tangible computer-readable storage medium whose contents include a program with instructions being executed on a processor so as to perform a method detecting host cell contaminants in a protein biotherapeutic product using sequential windowed acquisition tandem mass spectrometry. The method includes providing a system, wherein the system comprises one or more distinct software modules, and wherein the distinct software modules comprise a measurement module and a detection module.

The measurement module receives one or more measured product ion spectra of the plurality of product ion spectra from a tandem mass spectrometer. The tandem mass spectrometer performs sequential windowed acquisition on a protein biotherapeutic product sample by sequentially stepping a precursor mass window across a mass range, fragmenting transmitted precursor ions of each stepped precursor mass window, and analyzing product ions produced from the fragmented transmitted precursor ions. The sequential windowed acquisition is performed without any information about contaminating proteins before data acquisition. The sequential windowed acquisition produces a plurality of product ion spectra for the mass range.

The detection module compares the one or more measured product ion spectra to a library of host cell proteins, and detects one or more host cell contaminants by reporting host cell proteins from the library that match the one or more measured product ion spectra.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DESCRIPTION OF VARIOUS EMBODIMENTS

Computer-Implemented System

Figure 1:
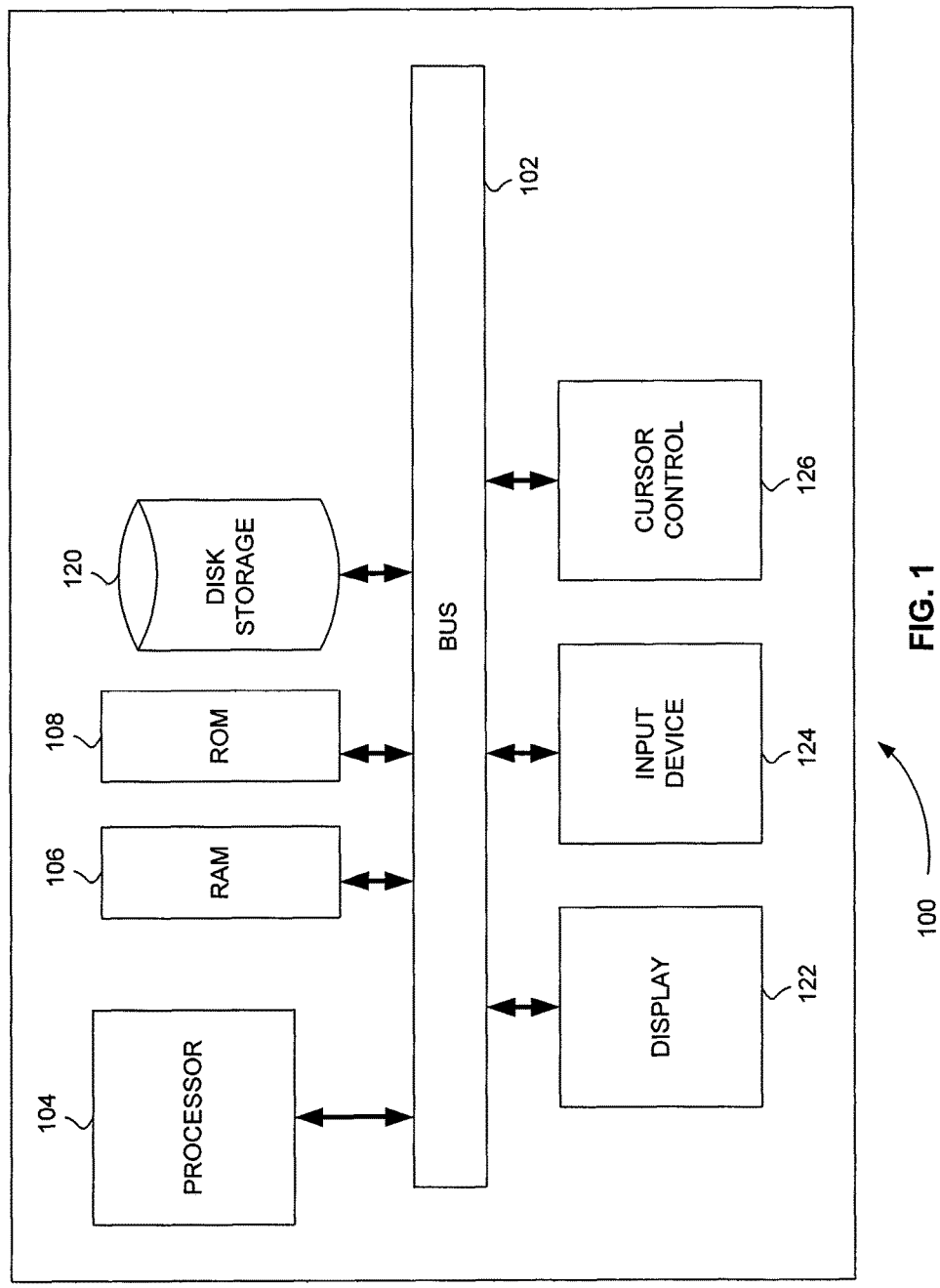
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Detecting Host Cell Protein Contaminants

As noted above, monoclonal antibodies (mAb) are target-oriented biotherapeutics that are used to treat an array of human diseases. mAbs are typically produced in biological systems, such as Chinese hamster ovary (CHO) or other cell lines. Heterogeneity of IgG proteins due to post-translational modifications (PTMs), sequence variants, degradation products, and contaminants (such as host cell proteins) must be characterized completely to understand purity, stability and potency of the mAb product, and to avoid immunogenicity. Mass spectrometry (MS) is a superior method for the characterization of mAbs.

In various embodiments, methods and systems provide a data-independent analysis approach that provides benefits over other MS strategies because the data-independent analysis approach captures comprehensive quantitative mass spectrometry/mass spectrometry (MS/MS or $MS^2$) chromatograms of every fragment ion from a given sample that can be mined extensively post-acquisition.

In various embodiments, methods and systems use sequential windowed acquisition (SWATH™) technology to obtain a quantitative measure of every fragment ion of every peptide in a trypsin digest of any protein biotherapeutic.

In various embodiments, methods and systems then mine the subsequent data for the presence of host cell proteins using a library constructed from the genome of the host cell organism or using a spectral library constructed from data dependent acquisition analysis of a host cell tryptic digest. By using quantitative mass spectrometry technologies the reactivity of a rabbit is moot. SWATH™ technology is superior for this application because one does not need to know about the contaminating proteins before data acquisition, and because a SWATH™ acquisition contains a complete quantitative record of all fragment ions of all peptides in a digest of a product at a given time it serves as a historical record as well.

In one exemplary experiment, 7 parts per million (weight: weight) of contaminant protein to product protein was detected by SWATH™ analysis.

In various embodiments, methods and system provide higher sensitivity, higher confidence in discovered contaminant spectra from having chromatograms of each fragment ion, as compared to discovery proteomics methods, such as information-dependent acquisition (IDA).

In various embodiments, methods and systems help resolve ownership of fragments of near-eluting near-isobaric compounds, whereas a conventional IDA method may only have one or two $MS^2$ spectra and no chromatogram.

In various embodiments, methods and systems provide at least two benefits as compared to multiple reaction monitoring (MRM) quantitation. First, a user/customer does not need to know exactly what he or she is looking for ahead of time, and there is no pre-acquisition method development. Furthermore, methods and systems capture fragment ion chromatograms for every fragment of every precursor ion visible to an instrument, so the resulting data contains a digital record of the current state of the product that can be mined later for contaminants that might be a concern at a later date.

In various embodiments, methods and systems provide higher confidence in the quality of a customer's products.

In various embodiments, methods and systems enable less reliance on temperamental antibody reagents to ensure the safety of injectable biotherapeutics products.

In various embodiments, methods and systems allow greater ability to track changes in the product over time quantitatively and faster reaction to problems with production, purification, and formulation of the product.

Host Cell Contaminants Detection System

Figure 2:
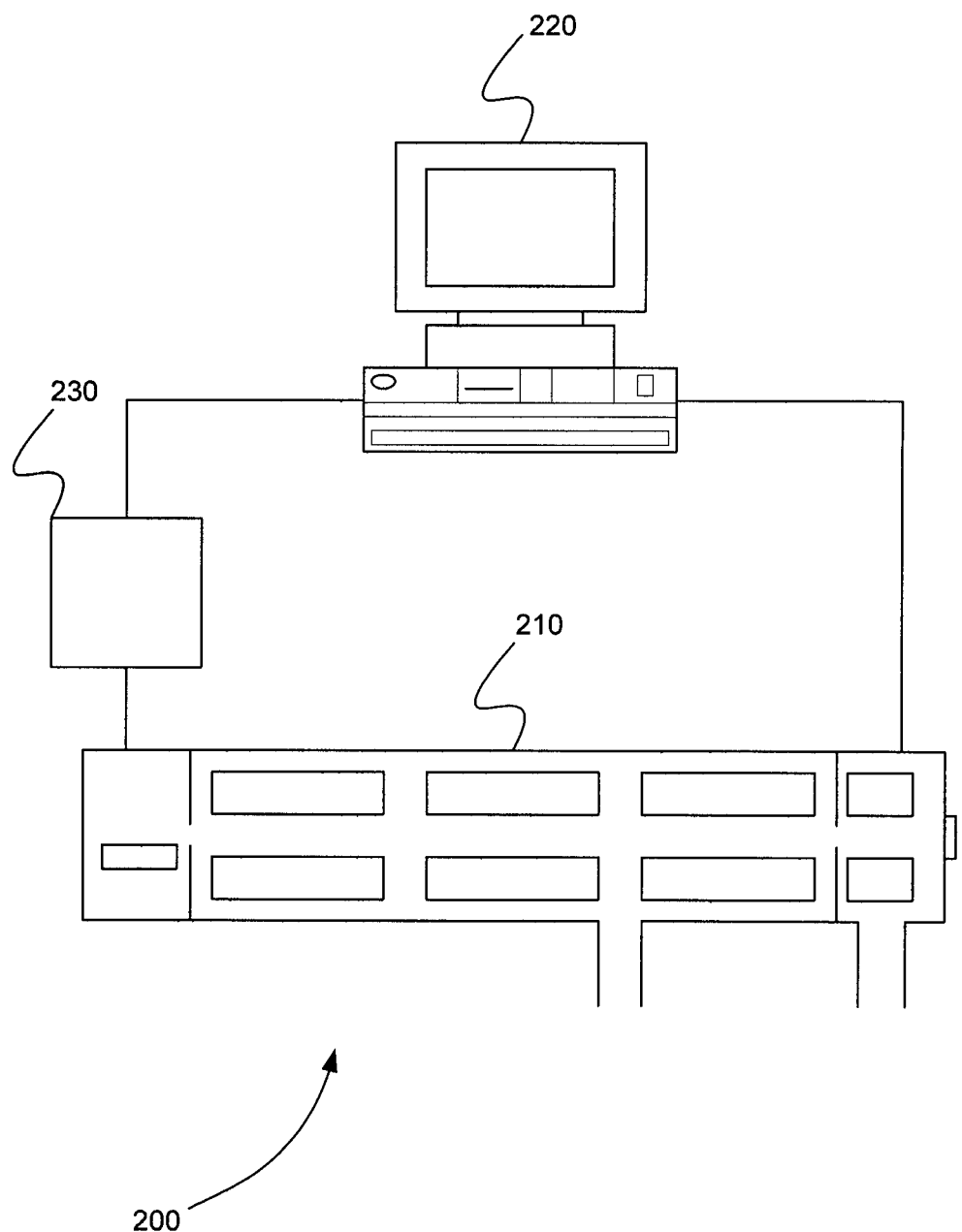
FIG. 2 is a schematic diagram showing a system for detecting host cell contaminants in a protein biotherapeutic product using sequential windowed acquisition tandem mass spectrometry, in accordance with various embodiments.

FIG. 2 is a schematic diagram showing a system 200 for detecting host cell contaminants in a protein biotherapeutic product using sequential windowed acquisition tandem mass spectrometry, in accordance with various embodiments. System 200 includes tandem mass spectrometer 210, processor 220, and separation device 230.

Tandem mass spectrometer 210 can include one or more physical mass filters and one or more physical mass analyzers. A mass analyzer of a tandem mass spectrometer can include, but is not limited to, a time-of-flight (TOF), quadrupole, an ion trap, a linear ion trap, an orbitrap, or a Fourier transform mass analyzer.

Tandem mass spectrometer 210 performs sequential windowed acquisition on a protein biotherapeutic product sample by sequentially stepping a precursor mass window across a mass range, fragmenting transmitted precursor ions of each stepped precursor mass window, and analyzing product ions produced from the fragmented transmitted precursor ions.

The sequential windowed acquisition is performed without any information about contaminating proteins before data acquisition and wherein the sequential windowed acquisition produces a plurality of product ion spectra for the mass range.

Processor 220 can be, but is not limited to, a computer, microprocessor, or any device capable of sending and receiving control signals and data from tandem mass spectrometer 210 and processing data. Processor 220 is in communication with tandem mass spectrometer 210, receives one or more measured product ion spectra of the plurality of product ion spectra from the tandem mass spectrometer, compares the one or more measured product ion spectra to a library of host cell proteins, and detects one or more host cell contaminants by reporting host cell proteins from the library that match the one or more measured product ion spectra.

In various embodiments, processor 220 performs quantitation on each product ion produced from the fragmented transmitted precursor ions and quantifies the one or more host cell contaminants detected.

In various embodiments, the library of host cell proteins is constructed from the genome of the host cell organism.

In various embodiments, the library of host cell proteins comprises spectral data and is constructed from data dependent acquisition analysis of a host cell tryptic digest.

In various embodiments, the protein biotherapeutic product sample comprises a monoclonal antibody (mAb) or one or more polyclonal antibodies.

In various embodiments, the host cell contaminant detection is performed without an enzyme-linked immunosorbent assay (ELISA) assay.

Tandem mass spectrometer 210 can also include a separation device 230. Separation device 230 can perform a separation technique that includes, but is not limited to, liquid chromatography, gas chromatography, capillary electrophoresis, or ion mobility. Tandem mass spectrometer 210 can include separating mass spectrometry stages or steps in space or time, respectively. Separation device 230 separates the sample from a mixture, for example. In various embodiments, separation device 230 comprises a liquid chromatography device and a product ion spectrum for each stepped precursor mass window is acquired within a liquid chromatography (LC) cycle time.

Host Cell Contaminants Detection Method

Figure 3:
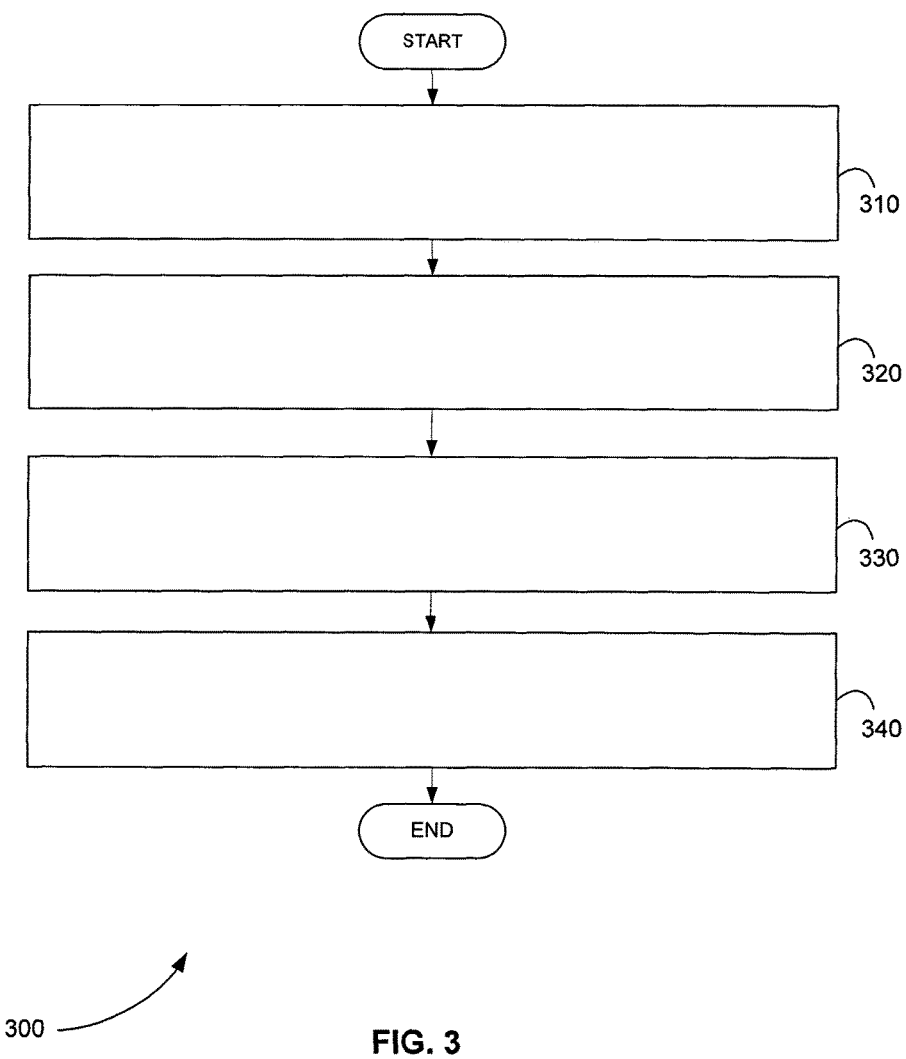
FIG. 3 is an exemplary flowchart showing a method for detecting host cell contaminants in a protein biotherapeutic product using sequential windowed acquisition tandem mass spectrometry, in accordance with various embodiments.

FIG. 3 is an exemplary flowchart showing a method 300 for detecting host cell contaminants in a protein biotherapeutic product using sequential windowed acquisition tandem mass spectrometry, in accordance with various embodiments.

In step 310 of method 300, sequential windowed acquisition is performed on a protein biotherapeutic product sample using a tandem mass spectrometer. The sequential windowed acquisition is performed by sequentially stepping a precursor mass window across a mass range, fragmenting transmitted precursor ions of each stepped precursor mass window, and analyzing product ions produced from the fragmented transmitted precursor ions. The sequential windowed acquisition is performed without any information about contaminating proteins before data acquisition. The sequential windowed acquisition produces a plurality of product ion spectra for the mass range.

In step 320, one or more measured product ion spectra of the plurality of product ion spectra are received from the tandem mass spectrometer using a processor.

In step 330, the one or more measured product ion spectra are compared to a library of host cell proteins using the processor.

In step 340, one or more host cell contaminants are detected by reporting host cell proteins from the library that match the one or more measured product ion spectra using the processor.

Host Cell Contaminants Detection Computer Program Product

In various embodiments, a computer program product includes a tangible computer-readable storage medium whose contents include a program with instructions being executed on a processor so as to perform a method for detecting host cell contaminants in a protein biotherapeutic product using sequential windowed acquisition tandem mass spectrometry. This method is performed by a system that includes one or more distinct software modules.

Figure 4:
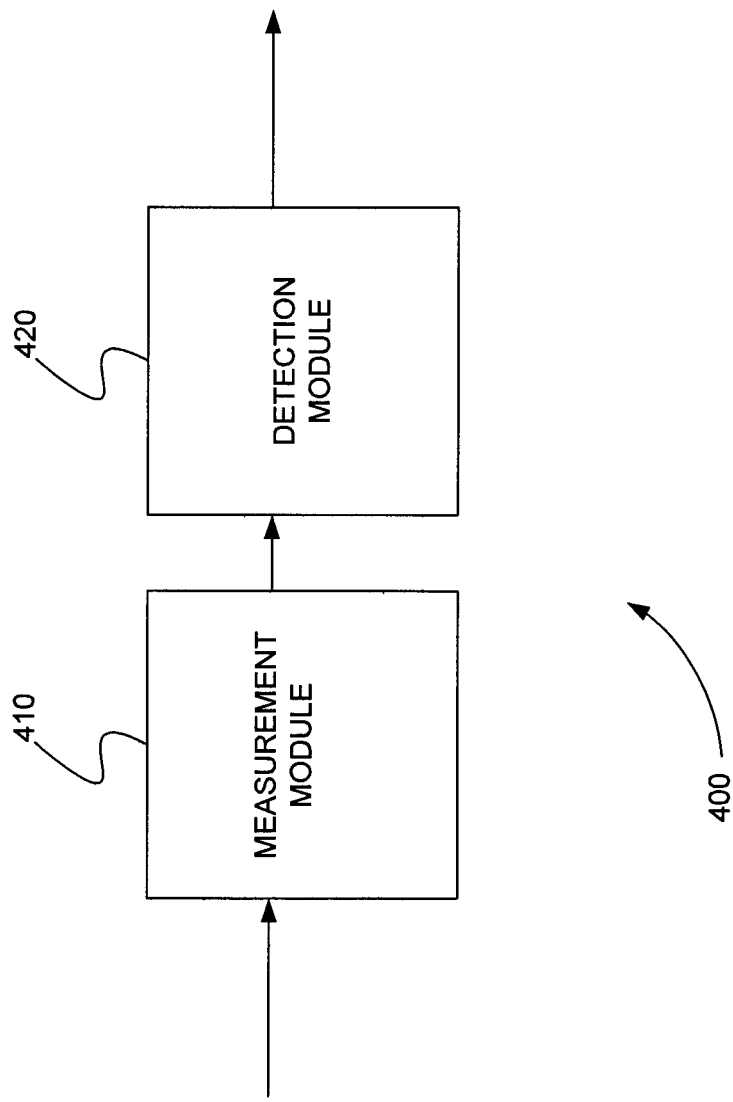
FIG. 4 is a schematic diagram of a system that includes one or more distinct software modules that performs a method for detecting host cell contaminants in a protein biotherapeutic product using sequential windowed acquisition tandem mass spectrometry, in accordance with various embodiments.

FIG. 4 is a schematic diagram of a system 400 that includes one or more distinct software modules that performs a method for detecting host cell contaminants in a protein biotherapeutic product using sequential windowed acquisition tandem mass spectrometry, in accordance with various embodiments. System 400 includes measurement module 410 and detection module 420.

Measurement module 410 receives one or more measured product ion spectra of the plurality of product ion spectra from a tandem mass spectrometer. The tandem mass spectrometer performs sequential windowed acquisition on a protein biotherapeutic product sample by sequentially stepping a precursor mass window across a mass range, fragmenting transmitted precursor ions of each stepped precursor mass window, and analyzing product ions produced from the fragmented transmitted precursor ions. The sequential windowed acquisition is performed without any information about contaminating proteins before data acquisition. The sequential windowed acquisition produces a plurality of product ion spectra for the mass range.

Detection module 420 compares the one or more measured product ion spectra to a library of host cell proteins, and detects one or more host cell contaminants by reporting host cell proteins from the library that match the one or more measured product ion spectra.

Data Examples

Figure 5:
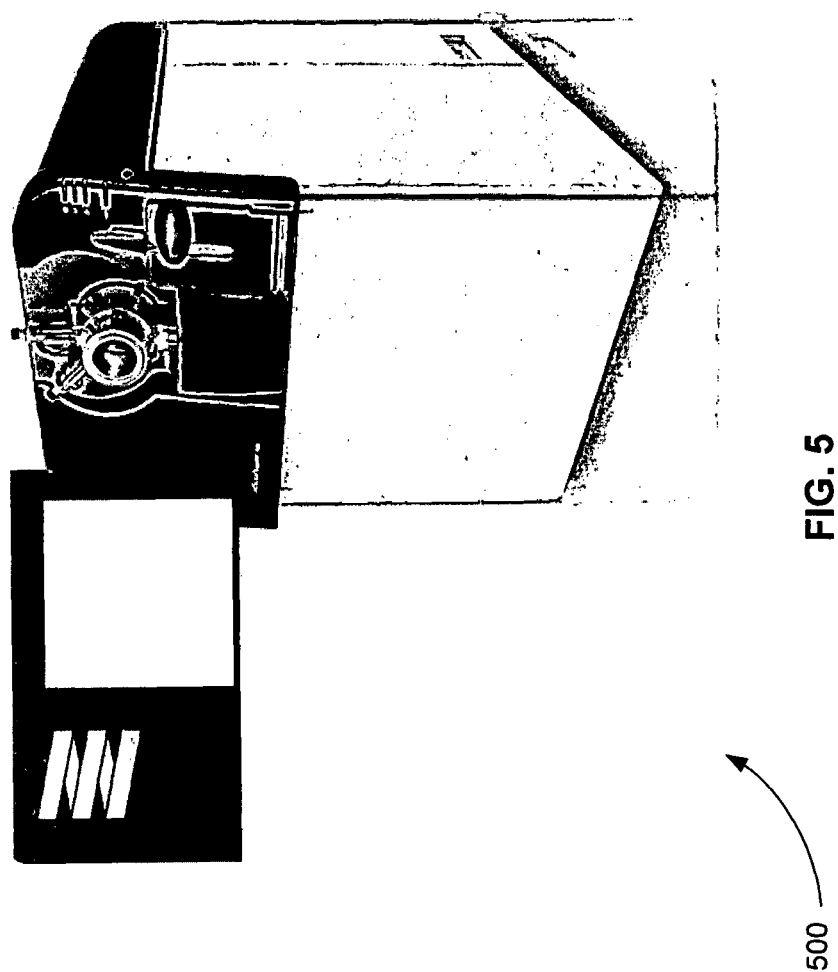
FIG. 5 illustrates an exemplary TripleTOF® 5600 system for protein characterization from complex proteomics samples, in accordance with various embodiments.

FIG. 5 illustrates an exemplary TripleTOF® 5600 system 500 for protein characterization from complex proteomics samples, in accordance with various embodiments.

Sample Preparation

In various embodiments, IgG1 mAb is reduced or alkylated and trypsin digested. A constant concentration of this digest is spiked with a range of Beta Galactosidase digest concentrations representing varying levels of a contaminating host cell protein.

Chromatography

In various embodiments, the sample is analyzed using the Eksigent Ekspert™ ultraLC 100-XL System. Varying amounts of lysate are loaded onto a column of, for example, 0.5 or 1.0 mm×10 cm ChromXP C18-CL 3 μm 120 Å. Elution gradients of, for example, 3-35% acetonitrile (0.1% formic acid) in 120 or 240 min are run.

Mass Spectrometry

In various embodiments, unmodified and spiked mAb digests are analyzed using, for example, a TripleTOF® 5600 system. One skilled in the art will appreciate that other types of mass spectrometry systems can equally be used.

In various embodiments, peptide identification is performed using an information dependent acquisition (IDA) liquid chromatography-MS/MS (LCMS/MS) method, for example. IDA LCMS/MS is described herein for illustration purposes only. One skilled in the art will appreciate that other types of mass spectrometry methods can equally be used.

In various embodiments, a data-independent acquisition strategy, such as SWATH™ acquisition, is performed in triplicate on each sample to acquire quantitative MS/MS chromatograms for every precursor between 400 and 1200 m/z using, for example, either 10 or 25 Da Q1 window width. SWATH™ acquisition is described herein for illustration purposes. One skilled in the art will appreciate that other types of data-independent acquisition techniques can equally be used.

In various embodiments, peak areas for extracted ion chromatograms are analyzed to provide a quantitative fingerprint of the chemical state of each peptide from the digested mAb. The TripleTOF® 5600 system's high sensitivity enables very fast MS/MS acquisition rates, allowing, for example, as low as 20 millisecond (ms) accumulation time for MS/MS in the IDA mode.

In various embodiments, to fully leverage the instrument speed and obtain the best depth of coverage, the IDA workflow can be optimized so that software overhead is minimized. In various embodiments, the IDA method includes a high resolution time-of-flight (TOF) MS survey scan followed by, for example, 20 MS/MS scans in a second with a minimum accumulation time of 50 msec. One skilled in the art will appreciate that different numbers of MS/MS scans can equally be applied.

In various embodiments, eluent from the column is sprayed using, for example, the Nanospray® III Source and heated interface. On skilled in the art will appreciate that other spaying methods can equally be used.

Data Processing

In various embodiments, all data are processed using, for example, ProteinPilot® software 4.5 with integrated false discovery rate (FDR) analysis. One skilled in the art will appreciate that other types of data processing software tools can equally be used.

In various embodiments, further data analysis is performed using, for example, the accompanying MS/MS$^{ALL}$ with SWATH™ acquisition MicroApp inside of PeakView® software, and MarkerView™ statistical analysis software. These software tools are described herein for illustration purposes. One skilled in the art will appreciate that other types of data processing software tools can equally be used.

In various embodiments, methods and systems for detecting host cell contaminants in a protein biotherapeutic product using sequential windowed acquisition tandem mass spectrometry utilize MS/MS$^{ALL}$ with SWATH™ acquisition, for example.

In various embodiments, MS/MS$^{ALL}$ with SWATH™ acquisition is a data-independent workflow enabled by, for example, Triple TOF® system technology that acquires high resolution quantifiable MS/MS data for all detectable analytes in a complex sample, in a single run. Triple TOF® system is described herein for illustration purposes only. One skilled in the art will appreciate that other types of acquisition systems can equally be used.

In various embodiments, SWATH™ acquisition uses wide isolation windows stepped across a mass range, collecting high resolution composite MS/MS spectra in a chromatographic time scale.

In various embodiments, MS/MS$^{ALL}$ with SWATH™ acquisition enables data processing by generation of post-acquisition fragment ion extracted ion chromatograms (XICs) at high resolution for quantitation with confirmation of identity.

In various embodiments, MS/MS$^{ALL}$ with SWATH™ acquisition enables quantitation and confirmation of everything in a sample, provides digital record of everything in a sample, and offers a single method for acquiring all the data.

SWATH™ Leverages High Resolution MS$^2$ for High Fidelity Quant

Figure 6:
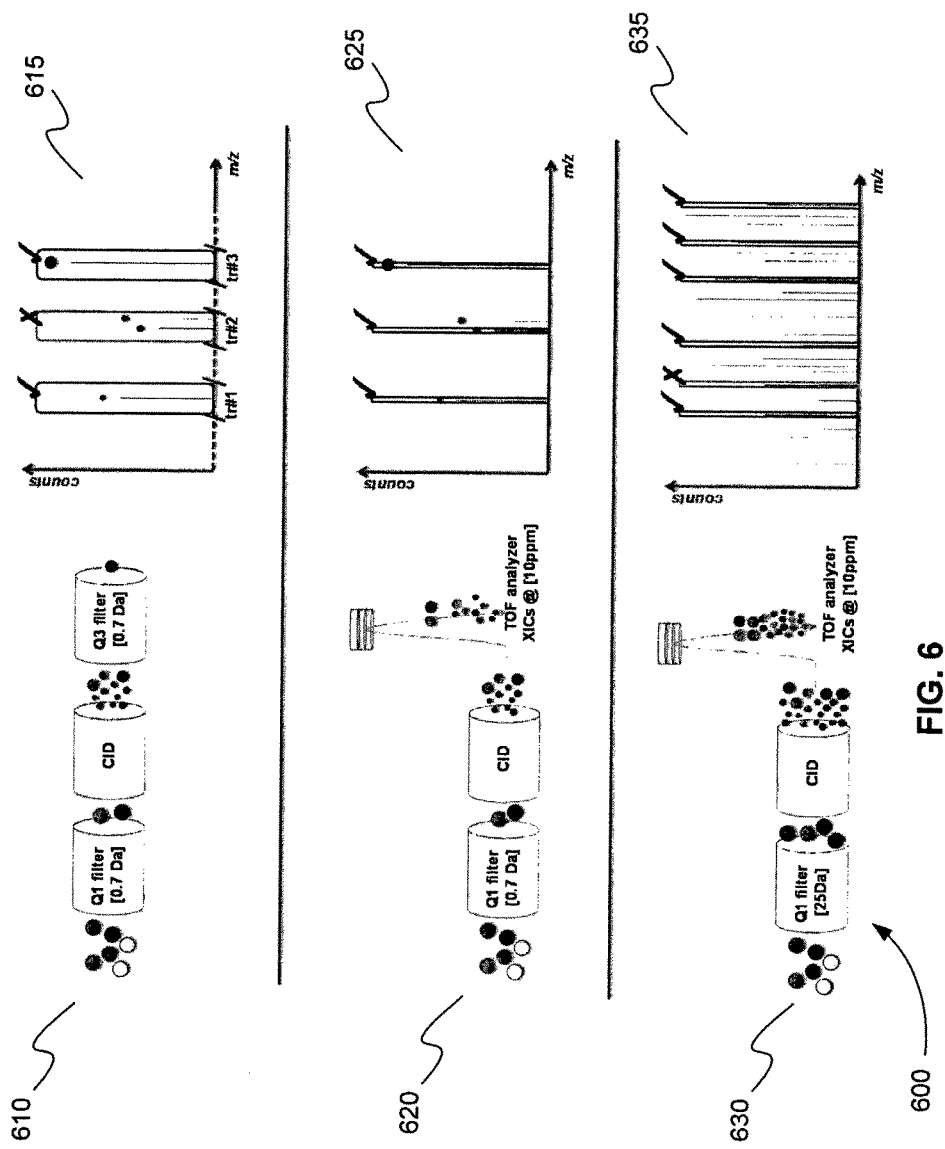
FIG. 6 is an exemplary SWATH™ scan modality overview, in accordance with various embodiments.

FIG. 6 is an exemplary SWATH™ scan modality overview 600, in accordance with various embodiments. Standard multiple reaction monitoring (MRM) quantitation 610 has 0.7 Da isolation on both quadrupoles, producing single reaction monitoring (SRM) traces that are shown as a pseudo-product ion representation 615. High resolution MRM or MRM$^{HR}$ 620, available on the TripleTOF® 5600 system, still scans Q1 at a width of 0.7 Da, but fragment ion chromatograms can be extracted from high resolution (>30K) MS/MS scans at much narrower widths (0.007 Da) enabling higher selectivity. MRM$^{HR}$ 620 produces high resolution and high mass accuracy product ion spectrum 625. SWATH™ technology 630 maximizes the use of MS/MS resolution, extracting narrow fragment ion chromatograms from fragmentation of a wide isolation in Q1 (~25 Da). SWATH™ technology 630 produces high resolution and high mass accuracy product ion spectrum 635.

Comprehensive Quantitation

Figure 7:
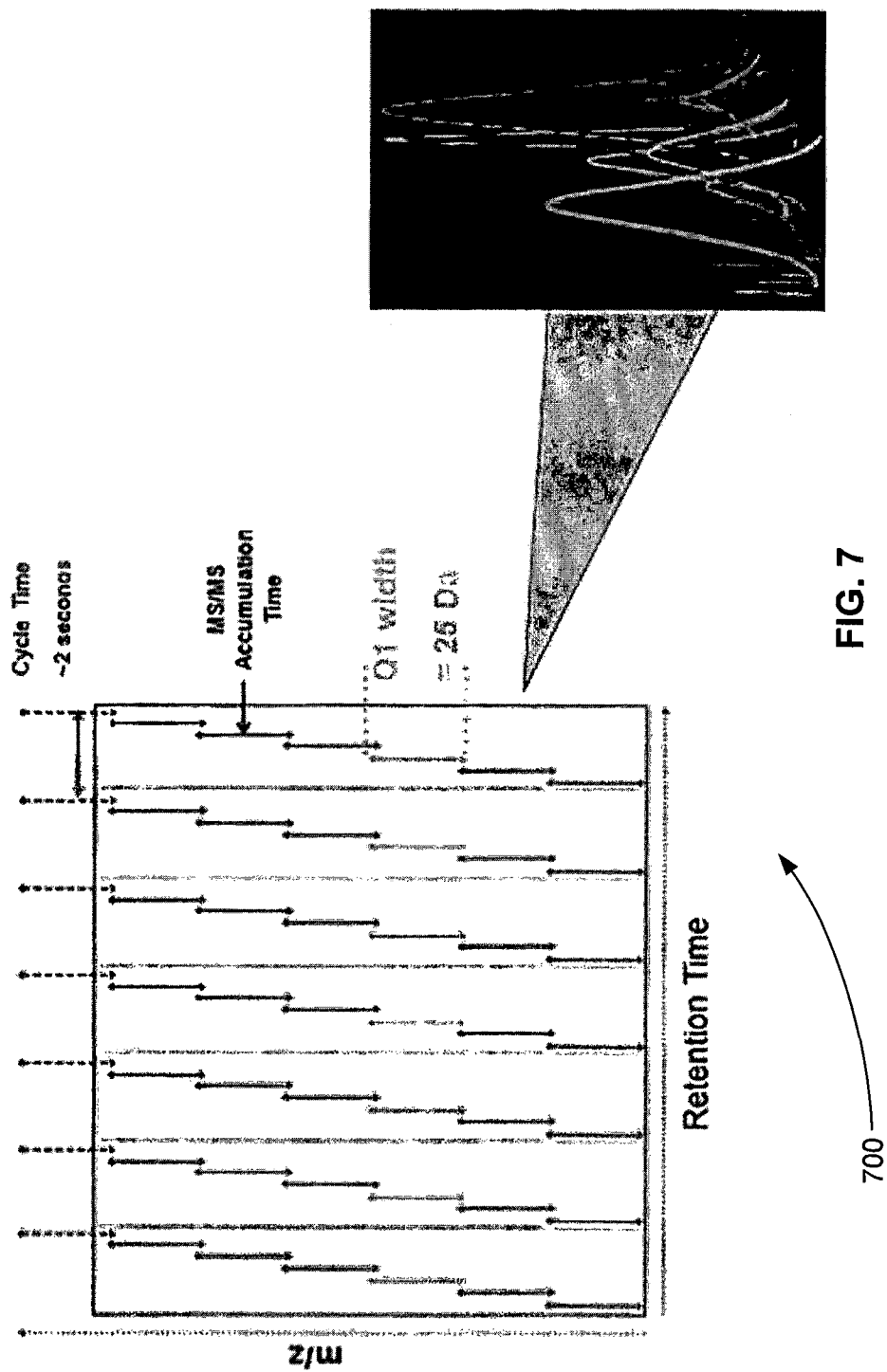
FIG. 7 illustrates an exemplary SWATH™ scan that obtains MS/MS data on all ions and can provide a comprehensive quantitation, in accordance with various embodiments.

FIG. 7 illustrates an exemplary SWATH™ scan 700 that obtains MS/MS data on all ions and can provide a comprehensive quantitation, in accordance with various embodiments. By stepping the mass range in 25 Da increments, fragment ion chromatograms of all observed ions are observed. A wide quadrupole 1 (Q1) isolation window is used (e.g., 25 Da or user defined). TripleTOF® 5600 system speed allows for full coverage of the mass range. High resolution XIC data is obtained for all fragment ions.

Results/Summary

In an experiment, in the data-independent workflow, the Q1 quadrupole was stepped at increments across the target mass range in 25 Da steps. Transmitted ions from the 25 Da wide window were fragmented in the collision cell and fragments are analyzed in the TOF MS analyzer at high resolution. This was done in an LC cycle time, such that MS/MS spectra were acquired on every peptide in a sample. High resolution XICs were then generated post-acquisition for quantification. Profiling the heterogeneity of this mAb, 95.8% of peptide sequence coverage was observed. Four deamidation sites and five oxidation sites were observed and their peptides quantified relative to unmodified forms. Comparison of peak areas from replicate analysis was typically within 5% cyclic voltammetry (CV). Additionally, data indicates that "host cell protein" can be detected at levels far below 0.01% contamination. Using the quantitative SWATH™ methodology, in a single sample run, MS/MS data can be acquired on every fragment ion from every precursor peptide ion between m/z of 400 and 1200. By examining the data retrospectively, the extent of PTM heterogeneity and host cell protein contamination can be quantified with MRM-like fidelity and sensitivity, without any up-front method development or foreknowledge of the PTM or contaminating protein.

Accessing Specificity of Targeted Acquisition Strategies

Figure 8:
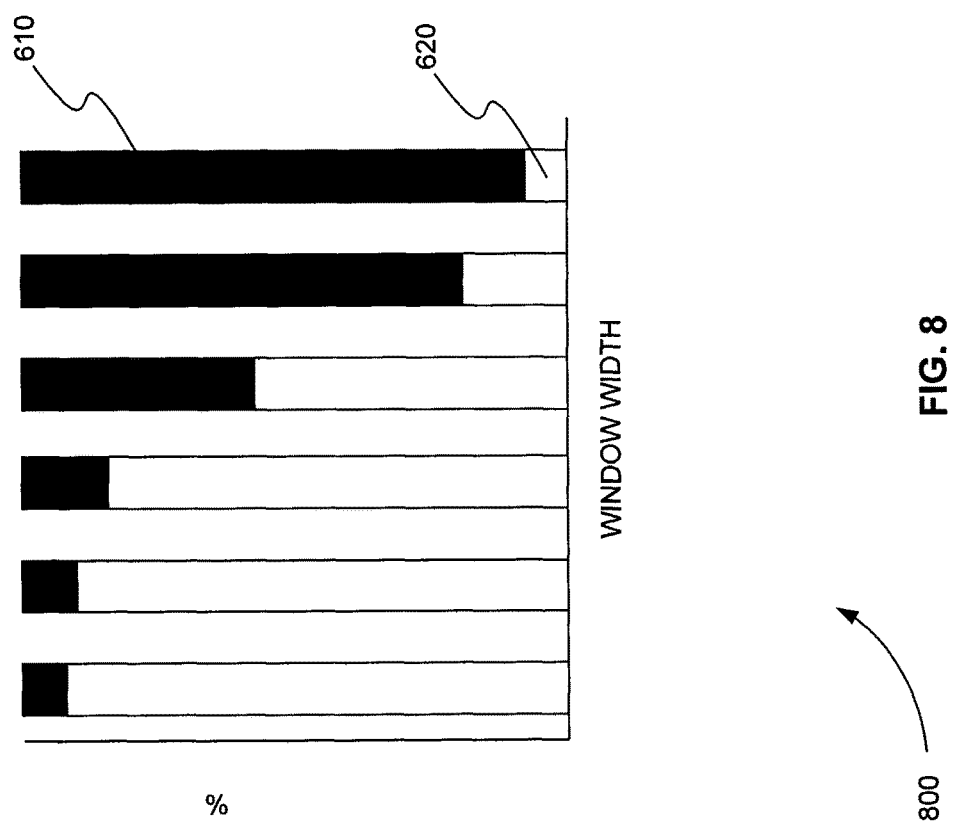
FIG. 8 is an exemplary plot showing how the percentage of peptides observable with 5 or more interference-free transitions varies with window widths for the precursor and fragment ion isolation, in accordance with various embodiments.

FIG. 8 is an exemplary plot 800 showing how the percentage of peptides observable with 5 or more interference-free transitions varies with window widths for the precursor and fragment ion isolation, in accordance with various embodiments. The black areas 610 depict the percentage of peptides with less than 4 interference-free transitions, and the white areas 620 depict the percentage of peptides with 5 or more interference-free transitions. SWATH™ is the only DIA technique that rivals MRM in terms of selectivity.

Referring to FIG. 8, the goal for quantification is to have multiple fragment ions per peptide to use for XIC generation and integration. In various embodiments, using peptides from a peptide repository, such as PeptideAtlas, the frequency of fragment ion interferences observed as a function of isolation and detection resolution is computed. As resolution decreases on isolation or detection, the number of peptides with five interference free XICs declines.

Single SWATH™ Acquisition Window

Figure 9:
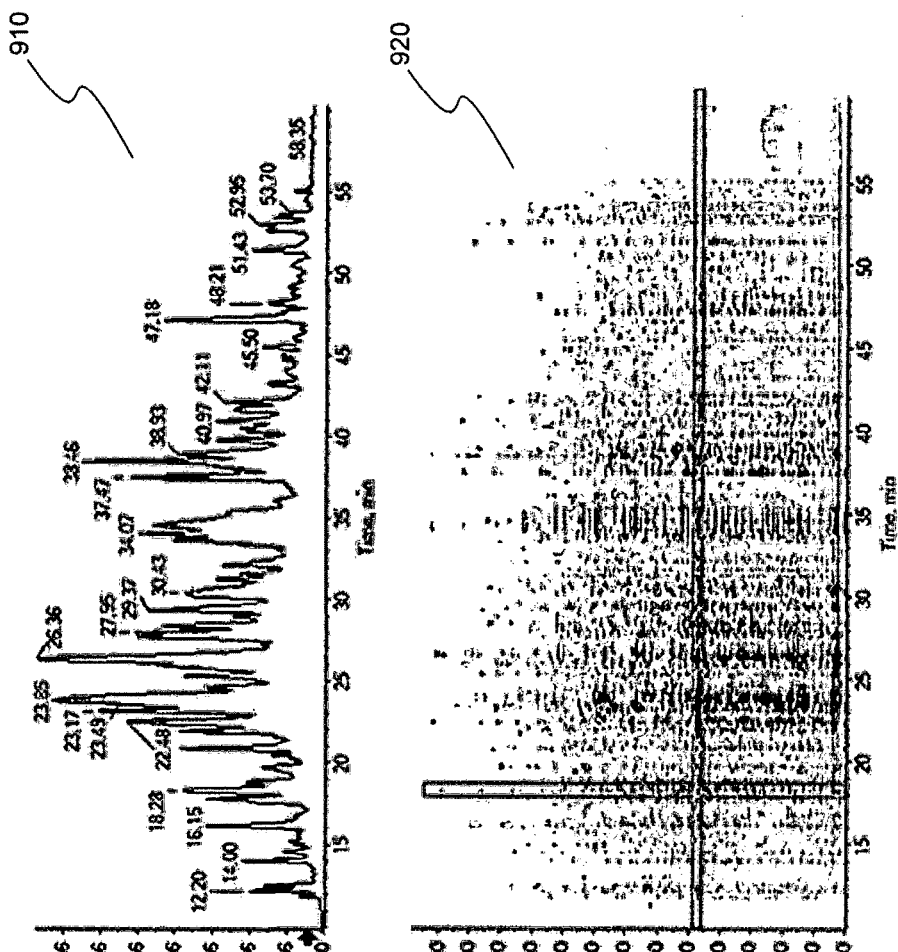
FIG. 9 is a collection of exemplary plots showing examples of SWATH™ data, in accordance with various embodiments.

FIG. 9 is a collection of exemplary plots 900 showing examples of SWATH™ data, in accordance with various embodiments. Specifically, FIG. 9 shows visual depiction of a single SWATH™ data set. Chromatogram 910 and heat map 920 are from an m/z ratio of 550-575 SWATH™. Inside this single acquisition there are 23 other three-dimensional data sets just like the above. In heat map 920 shown in FIG. 9, the X axis represents time, the Y axis is m/z ratio, and intensity is represented by color. The horizontal box indicates the q1 selection window, and all ions outside that box are fragments. Each vertical stripe is an MS/MS spectrum inside the vertical box, for example.

Referring to FIG. 9, in various embodiments, methods and systems use 25 Da window to cover the peptide mass range in a LC time frame. FIG. 9 also shows three-dimensional data, and MS/MS on all precursors between 550-575 mass-to-charge (m/z) ratios.

PeakView® SWATH™ Analysis Tool

Figure 10:
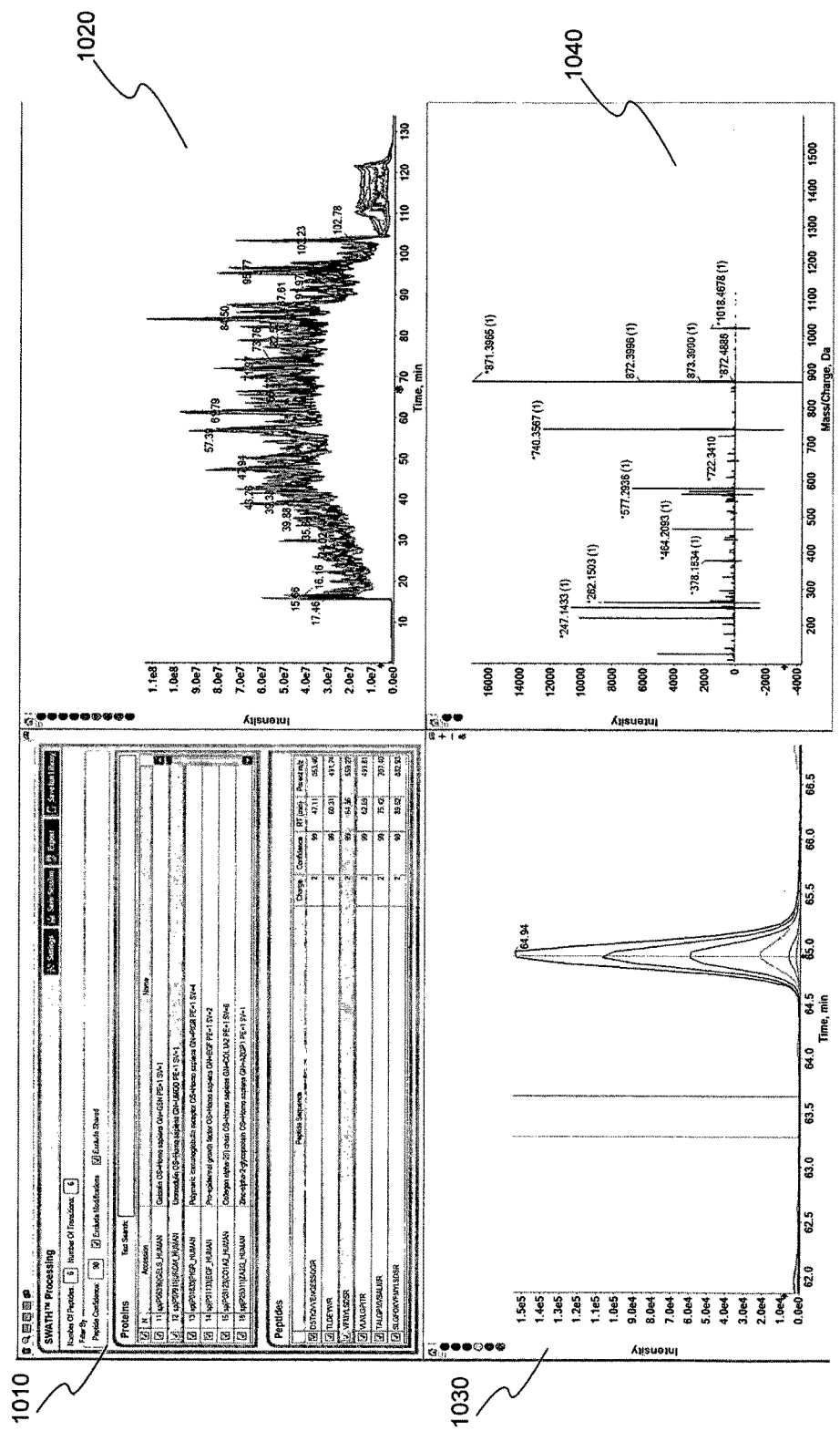
FIG. 10 is a collection of exemplary plots showing SWATH™ analysis software, in accordance with various embodiments.

FIG. 10 is a collection exemplary plots 1000 showing SWATH™ analysis software, in accordance with various embodiments. Top left pane 1010 is an exemplary list of proteins and peptides from an ion library, such as a Protein Pilot™ group file from an IDA run of the measured sample. Top right pane 1020 of FIG. 10 is an exemplary plot showing exemplary total ion current (TIC) chromatograms of each SWATH™ data file. Bottom left pane 1030 is an exemplary plot showing exemplary XIC chromatograms of six fragment ions from the peptide selected in top left pane 1010. Bottom right pane 1040 is an exemplary mirror plot showing the MS/MS spectrum collected at the top of the chromatogram in bottom left pane 1030 over the spectrum from the ion library.

SWATH™ Analysis: MarkerView™ Results—Protein Data

In various embodiments, principal component variable grouping analysis can be performed using SWATH™ data. Using MarkerView™ software, for example, trends in protein concentration changes can easily be visualized and tracked through plots. It is especially important to have powerful software when tracking the concentration of every single peptide in a complex data set.

In various embodiments, SWATH™ analysis is capable of detecting contaminants with MRM level sensitivity and fidelity, without having to know what was being looked for in the beginning of the assay.

Conclusions

MS/MS$^{ALL}$ with SWATH™ acquisition is a novel data-independent acquisition strategy that provides comprehensive high resolution MS/MS data for all detectable ions, high quality quantitation similar to MRM with no method development, and easy and retrospective data interrogation.

In various embodiments, SWATH™ data can be processed by, for example, PeakView® software and MarkerView™ software, or extracted for use with third party informatics tools. One skilled in the art will appreciate that other types of data processing software tools can equally be used.

In various embodiments, SWATH™ acquisition is ideal for quantifying protein contaminants in biologic protein products.

In various embodiments, methods and systems provide quantitative sensitivity and fidelity rivaling enzyme-linked immunosorbent assay (ELISA) without safety concerns of reagent preparation, since not everything that produces a reaction in human produces a reaction in rabbit.

In various embodiments, methods and systems capture a digital record of all fragments of all peptides in a protein product. This can be used to track changes over time and the data can serve as a digital archive of the current state of a sample at a given time. This data can be retroactively mined for any protein contaminant concerns in the future.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for detecting host cell contaminants in a protein biotherapeutic product using sequential windowed acquisition tandem mass spectrometry, comprising:
    a tandem mass spectrometer that is programmed to perform sequential windowed acquisition on a protein biotherapeutic product sample without any information about contaminating proteins before data acquisition and without pre-acquisition method development by sequentially stepping a precursor mass window across a mass range, fragmenting transmitted precursor ions of each stepped precursor mass window, and analyzing product ions produced from the fragmented transmitted precursor ions, wherein the sequential windowed acquisition produces a plurality of product ion spectra for the mass range; and
    a processor in communication with the tandem mass spectrometer that is programmed to
        receive one or more measured product ion spectra of the plurality of product ion spectra from the tandem mass spectrometer,
        compare the one or more measured product ion spectra to a library of host cell proteins, and
        detect one or more host cell contaminants by reporting host cell proteins from the library that match the one or more measured product ion spectra.

2. The system of claim 1, wherein the processor is further programmed to perform quantitation on each product ion produced from the fragmented transmitted precursor ions and quantifies the one or more host cell contaminants detected.

3. The system of claim 1, wherein the library of host cell proteins is constructed from the genome of the host cell organism.

4. The system of claim 1, wherein the library of host cell proteins comprises spectral data and is constructed from data dependent acquisition analysis of a host cell tryptic digest.

5. The system of claim 1, wherein the protein biotherapeutic product sample comprises a monoclonal antibody (mAb) or one or more polyclonal antibodies.

6. The system of claim 1, further comprising a separation device that separates the sample from a mixture.

7. The system of claim 6, wherein the separation device comprises a liquid chromatography device and a product ion spectrum for each stepped precursor mass window is acquired within a liquid chromatography (LC) cycle time.

* * * * *

UNITED STATES PATENT AND TRADEMARK OFFICE
CERTIFICATE OF CORRECTION

PATENT NO.       : 9,891,203 B2
APPLICATION NO.  : 14/889138
DATED            : February 13, 2018
INVENTOR(S)      : Eric Johansen Page 1 of 1

It is certified that error appears in the above-identified patent and that said Letters Patent is hereby corrected as shown below:

On the Title Page

Item (54) and in the Specification, Column 1, Line 1, in the title, "SWATH #" should be changed to --SWATH™--

Signed and Sealed this
Twenty-fifth Day of June, 2019

Andrei Iancu
*Director of the United States Patent and Trademark Office*